United States Patent [19]

Hattori

[11] Patent Number: 4,640,288

[45] Date of Patent: Feb. 3, 1987

[54] ADHESIVE PAD FOR USE ON HUMAN BODY

[75] Inventor: Morihisa Hattori, Nishinomiya, Japan

[73] Assignee: Nikko Kakouzai Co., Ltd., Osaka, Japan

[21] Appl. No.: 654,630

[22] Filed: Sep. 26, 1984

[30] Foreign Application Priority Data

Sep. 28, 1983 [JP] Japan .................................. 58-181209

[51] Int. Cl.⁴ ............................................. A61J 13/00
[52] U.S. Cl. .................................................... 128/505
[58] Field of Search ................ 128/505, 480, 477, 150

[56] References Cited

U.S. PATENT DOCUMENTS 1,783,512 12/1930 Mather ................................. 128/505
4,333,471 6/1982 Nakai ................................... 128/505

Primary Examiner—Doris L. Troutman
Attorney, Agent, or Firm—Armstrong, Nikaido, Marmelstein & Kubovcik

[57] ABSTRACT

An adhesive pad is disclosed herein for use on human body, particularly suitable for women's use as a nipple cover or protector for afflicted portions such as the heel suffering shoe sore. The adhesive pad comprises a flexible sheet of diaphanous plastic material and an adhesive coating formed on the periphery of the underside of the sheet so as to define inside thereof a non-adhesive and translucent area which is in adhesive-free covering contact with a particular portion on the body to be protected. Accordingly, the portion of the body can be seen through the adhesive pad so that the pad itself can be undiscerned to present natural appearance of the body as protecting the portion that portion from being rubbed or injured.

4 Claims, 7 Drawing Figures

ADHESIVE PAD FOR USE ON HUMAN BODY

BACKGROUND OF THE INVENTION

1. Field of the Invention

The present invention is directed to an adhesive pad for use on human body, and more particularly to an adhesive pad adapted in use to protect a particular portion on the human body, for example, the nipple of a female person or afflicted portion on the human skin from being rubbed or irritated by her dress or other wearing articles.

2. Description of the Art

There has been increased tendency for women, particularly for the younger women to wear thin and see-through dress or other garments without a brassier thereunder and it has been preferred by those women not to conceal their nipples unnaturally when wearing the see-through clothes. However, such clothes when directly fitted on the breast may sometimes injure the nipple as rubbing or irritating the same. For this reason it has been an usual practice to cover the nipples by means of widely available adhesive bandages or the like covering tapes with a padding material of soft fabric material. Such covering eventually conceals the nipple and accordingly presents an unnatural appearance of the breast seen through the garment. Thus, there is a certain need by the women wearing the see-through dress or other garment for protecting the nipple by means of a covering which is undiscerned and unnoticeable of itself. Apart from the breast, there are still other parts on the skin, for example, the heel suffering the shoe sore, which are to be protected by a suitable covering but require such covering not to be unduly remarked for the sake of appearance. In this respect also, the conventional adhesive bandage or like adhesive tape with the fabric padding material fail to meet the above requirement.

SUMMARY OF THE INVENTION

The above inconvenience has been eliminated by the present invention which discloses a unique and improved adhesive pad for use on the human body comprising a flexible sheet of diaphanous plastic material and an adhesive coating formed on the underside of the sheet. Said adhesive coating is provided along the periphery of the sheet to define inside thereof a non-adhesive and smooth surface area which is adapted to be adhesive-free contact with a particular portion on the human body and which allows that portion covered thereby to be seen therethrough. With this arrangement, the flexible sheet can be easily conform to the contour of the particular portion of the body to be protected and be easily secured by the adhesive coating thereto with the non-adhesive area being in direct covering contact with that portion, whereby the portion covered by the non-adhesive area will be rather in smooth contact with the pad so as not to suffer injurious effect therefrom. This is most suitable when the adhesive pad of the present invention is applied as a nipple cover for women wearing thin and see-through dress or other garment to cover the nipple by said non-adhesive and translucent area, since the nipple can not be unnaturally concealed beneath the clothes and is not uncomfortably adhered to the pad. In addition to the above, the adhesive pad of the present invention finds itself useful to be applied for protecting the heel suffering the shoe sore. In this application, the pad will not be remarkably seen due to its diaphanous nature while the afflicted portion of the skin is not adhered to the pad to thereby be free from being subject to rubbing or irritating action, which would adversely affect the afflicted portion.

Accordingly, it is a primary object of the present invention to provide an adhesive pad for use on human body which is capable of protecting a particular portion on the body without impairing natural appearance of the body surface.

In a preferred embodiment, said non-adhesive and translucent area is formed by laminating a diaphanous and flexible film on the flexible sheet through the medium of an adhesive layer applied on the entire surface of the underside of the sheet. Said film is sized to be less than the sheet so that when laminated it leave therearound the adhesive layer exposed to define said adhesive coating surrounding the film. The film thus laminated on the flexible sheet serves to strengthen the central portion of the adhesive pad to some extent so as to give sufficient resistivity against crumpling prior to its use while rendering the pad to retain enough flexibility of easily conforming to the contour of the body surface. Besides, the above lamination structure can facilitate the manufacture of the adhesive pad having the adhesive coating only at the marginal portion thereof.

It is therefore another object of the present invention to provide an adhesive pad for use on human body which can be easily applied as well as can be manufactured without difficulty or at a relative low cost.

Said adhesive coating is protected by a pair of release paper which are arranged to fully cover the underside of the sheet with adjacent edges thereof overlapped one on the other. Thus, just prior to the application of the pad to the particular portion on the body, the release papers can be readily peeled off simply by pulling the one paper overlapping the other and then pulling the other away from the adhesive coating, assuring easy and fast application of the pad.

It is therefore a further object of the present invention to provide an adhesive pad which is easy to be applied onto the body.

In the embodiment, the flexible sheet is made pale flesh colored so as to be well blended into the skin of the body for the purpose of effectively making the pad unnoticeable, which is a still another object of the present invention.

These and other objects of the present invention will be more apparent from the following detailed description of the preferred embodiment when taken in conjunction with the accompanying drawings.

DETAILED DESCRIPTION OF THE EMBODIMENT

Figure 1:
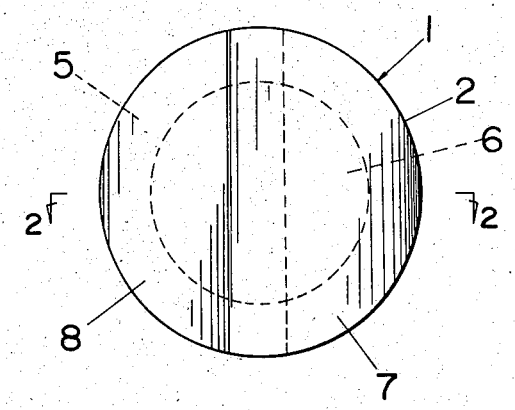
FIG. 1 is a plane view of an adhesive pad in accordance with a preferred embodiment of the present invention.
Figure 2:
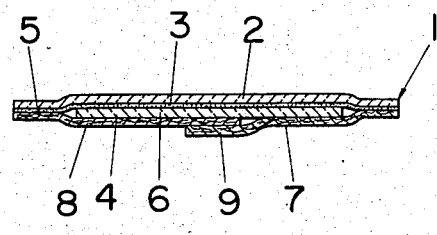
FIG. 2 is a cross section taken along line 2—2 of FIG. 1.

Referring now to FIGS. 1 and 2, there is illustrated an adhesive pad 1 for use on human body in accordance with a preferred embodiment of the present invention. The adhesive pad 1 includes a flexible sheet 2 of diaphanous plastic material which is made of, for example, a transparent polyvinyl chloride sheet and is tinted in pale flesh color or pale yellowish pink. The sheet 2 has a thickness of as less as 0.07 mm for presenting enough flexibility and is circular in shape suitable for use as a nipple cover. A number of tiny perforations (not shown) are formed in the sheet 1 for providing the sheet 1 with air permeability. Applied to the entire surface of one side or underside of the sheet 2 is an adhesive layer 3 of 0.05 mm thick. The adhesive employed is a pressure sensitive one commonly used on the well known adhesive bandage and adheres quickly and securely to the skin.

A flexible film 4 of diaphanous plastic material of circular shape but smaller than the sheet 2 is centrally disposed on the sheet 1 as being adhered firmly to said adhesive layer 3 so as to leave the peripheral portion of said adhesive layer 3 exposed around the film 4, thus defining an annulus of an adhesive coating 5 surrounding the film 4 by which the pad 1 is attached to the skin of the body. This diaphanous film 4 is made of a plastic material, for example, a transparent polyethylene film to retain the center portion of the pad 1 translucent and as well to form on the center portion of the sheet 1 a non-adhesive area 6 presenting a smooth surface which is to be in direct covering contact with a nipple or other particular portion on the body to be protected thereby so that the portion on the body covered by the film 4 will not be rubbed or irritated thereby. The film 4 has a thickness of 0.10 mm, a little greater than the sheet 1 to strengthen the central portion of the pad 1 to some extent for preventing the crumpling of the pad 1 and therefore the self-adhereing thereof due to the crumpling just prior to its application on the skin, while retaining enough flexibility for easily conforming to the contour of the portion of the body to be protected thereby.

Figure 3A:
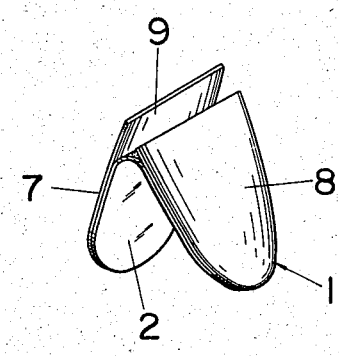
FIGS. 3A and 3B are perspective views showing the manner for peeling off release papers attached to the above pad.
Figure 3B:
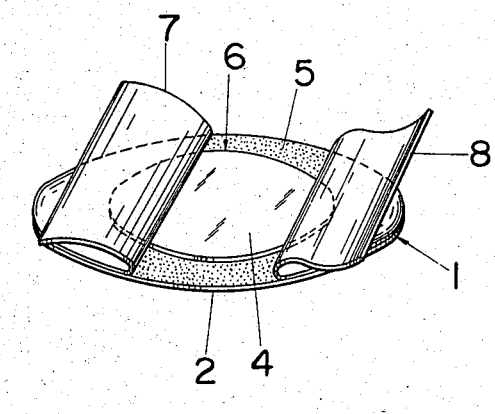

A pair of protective release papers 7 and 8 are removably adhered to said adhesive coating 5 in such a manner as to fully cover the entire undersurface of the pad 1 or the non-adhesive area 6 plus said adhesive coating 5 with the adjacent edges thereof overlapped one on the other. That is, one of the papers 7 and 8 is dimensioned to be larger than the other to have at its straight edge portion an integral pull tab 9 overlapping the edge portion of the other. Thus, the peeling of the release papers 7 and 8 can be easily done by firstly pulling the tab 9 of one paper 7 away from the adhesive coating 5 and then pulling the other paper away therefrom with holding the portion adjacent said non-adhesive area 6. And this peeling can be done much easier by bending the pad 1 at the time of pulling the release papers 7 and 8, as shown in FIG. 3A.

Figure 4:
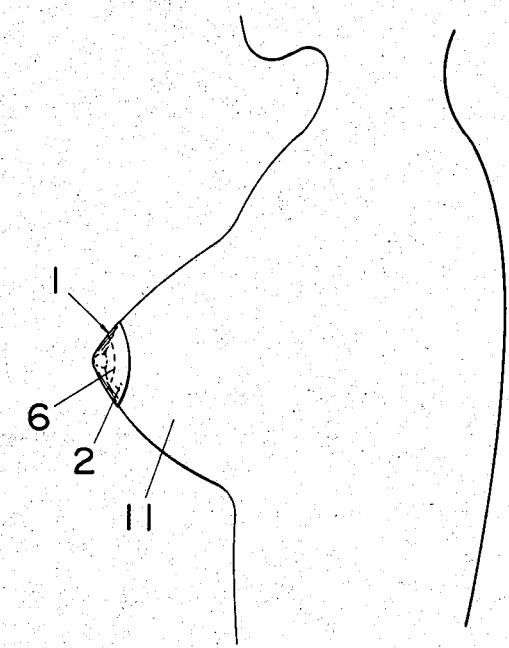
FIG. 4 is a side view showing an application of the above pad as a nipple cover.

FIG. 4 shows a typical application of the above pad for protecting the nipple of a women wearing a thin and see-through dress or other garment thereon. The pad 1, after being removed of the release papers 7 and 8, is placed centrally against her nipple as pressing the adhesive coating 3 against the breast 11 around the nipple for securing the pad 1 to the breast 11 such that the nipple is in direct covering contact with said non-adhesive area 6 or the smooth surface of the film 4. The nipple thus covered is protected from being rubbed or irritated by her clothes while the pad 1 well merges into her skin to be rendered unnoticeable, whereby when wearing the see-through clothes the nipple can be seen through the pad 1 and the clothes to present the natural appearance of her breast. This accords with the recent fashion preferred by women wearing such see-through dress or other garment without a brassier thereunder while retaining to protect the nipple from being rubbed or irritated thereby.

Figure 5:
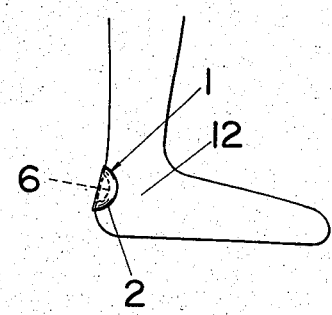
FIG. 5 is a side view showing another application of the above pad as a protector for the heel suffering the shoe sore.

Besides the above application as the nipple cover, the adhesive pad 1 of the present invention can find another useful use as a protector for the heel 12 suffering shoe sore, as shown in FIG. 5. In this application, the afflicted part on the heel is likewise in direct covering contact with the non-adhesive area 6 or the smooth surface of the film 4 so that it can be protected under the pad 1 without being subject to further rubbing action, while the pad 1 of translucent nature renders itself unnoticeable with or without wearing a pantihose or other see-through stocking thereon.

Figure 6:
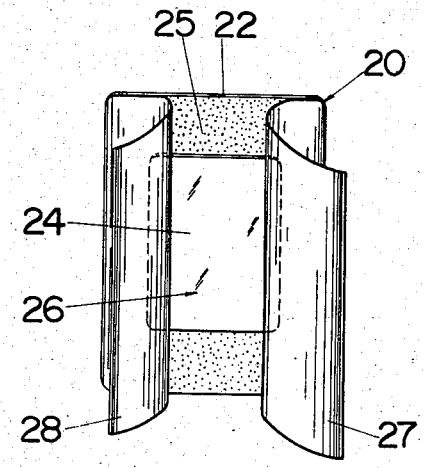
FIG. 6 is a perspective view of a modification of the above embodiment with release papers partially removed.

FIG. 6 shows a modification of the above embodiment which is similar in construction to the above embodiment except that a pad 20 is rectangularly shaped. The like flexible sheet 22, flexible film 24 and release papers 27 and 28 are correspondingly shaped into a rectangular configuration, and the like adhesive coating 25 is formed along the periphery of the sheet 22. This rectangular pad 20 is rather suitable for use on said heel, however, the adhesive pad of the present invention should not be limited to those shapes shown in the FIGS. 1 and 6, and can be made in various other shapes depending on the particular portion of the body to be protected.

Although the present invention discloses only one embodiment to define on the central portion of the flexible sheet the non-adhesive area as well as to define therearound the adhesive coating by laminating the flexible film thereon, the non-adhesive area can be made on the central portion of the sheet by exclusively applying adhesive on the peripheral portion of the underside of the sheet.

What is claimed is:

1. An adhesive pad for use on human body which comprises:
    a flexible sheet of diaphanous plastic material,
    an adhesive layer applied onto the entire underside of the sheet, and
    a flexible film of diaphanous plastic material laminated on said adhesive layer, said film having less planar dimensions less than the sheet and being centrally disposed thereon so as to leave said adhesive layer exposed therearound, said exposed adhesive layer defining an annulus of adhesive coating on the marginal portion of the sheet for securing the pad onto a selected area on the human body and defining inside thereof a non-adhesive and translucent area, said film having thereon a smooth surface which is adapted to be in adhesive-free contact with the portion on the human body, and said non-adhesive and translucent area allowing that portion of the body covered thereby to be seen through the lamination of the sheet and the film.

2. The adhesive pad as set forth in claim 1, further including a pair of protective release papers which are removably attached to said adhesive coating with adjacent edge portions thereof overlapped one on the other in such a way as to fully cover the underside of the sheet.

3. The adhesive pad as set forth in claim 1, wherein said diaphanous sheet is tinted in a pale flesh color and the film is transparent.

4. The adhesive pad as set forth in claim 1, wherein said flexible film is a transparent polyethylene film.

* * * * *